(12) United States Patent
Genova et al.

(10) Patent No.: US 6,779,520 B2
(45) Date of Patent: Aug. 24, 2004

(54) BREATH ACTUATED DRY POWDER INHALER

(75) Inventors: Perry A. Genova, Chapel Hill, NC (US); Keith Wakefield, Clayton, NC (US)

(73) Assignee: IEP Pharmaceutical Devices Inc., Raleigh, NC (US)

( * ) Notice: Subject to any disclaimer, the term of this patent is extended or adjusted under 35 U.S.C. 154(b) by 0 days.

(21) Appl. No.: 10/016,723

(22) Filed: Oct. 30, 2001

(65) Prior Publication Data

US 2003/0079743 A1 May 1, 2003

(51) Int. Cl.$^7$ ............................................. A61M 11/00
(52) U.S. Cl. ............................... 128/200.22; 128/203.15
(58) Field of Search ................... 128/203.12, 203.15, 128/200.22, 200.23, 203.21, 205.21; 604/38; 222/636

(56) References Cited

U.S. PATENT DOCUMENTS

| | | | | |
|---|---|---|---|---|
| 606,240 A | * | 6/1898 | Prescott | 239/331 |
| 865,022 A | * | 9/1907 | Dorment | 128/200.22 |
| 905,087 A | * | 11/1908 | Mallory | 128/200.22 |
| 923,822 A | * | 6/1909 | Dorment | 128/200.22 |
| 1,301,149 A | * | 4/1919 | Marshall | 111/7.4 |
| 1,752,956 A | * | 4/1930 | Lex | 222/633 |
| 3,144,867 A | * | 8/1964 | Trupp et al. | 433/88 |
| 3,157,179 A | * | 11/1964 | Paullus et al. | 128/200.23 |
| 3,187,748 A | * | 6/1965 | Mitchell et al. | 128/200.23 |
| 3,456,646 A | * | 7/1969 | Phillips et al. | 128/200.23 |
| 3,605,738 A | * | 9/1971 | Ciranna | 128/200.23 |
| 3,900,138 A | * | 8/1975 | Phillips | 222/340 |
| 4,796,614 A | * | 1/1989 | Nowacki et al. | 128/200.14 |
| 5,033,463 A | | 7/1991 | Cocozza | |
| 5,056,511 A | * | 10/1991 | Ronge | 128/200.14 |
| 5,113,855 A | * | 5/1992 | Newhouse | 128/203.12 |
| 5,201,308 A | * | 4/1993 | Newhouse | 128/203.15 |
| 5,284,133 A | * | 2/1994 | Burns et al. | 128/200.23 |
| 5,297,542 A | * | 3/1994 | Bacon | 128/200.14 |
| 5,323,936 A | * | 6/1994 | Wolter et al. | 222/401 |
| 5,388,572 A | * | 2/1995 | Mulhauser et al. | 128/203.15 |
| 5,447,150 A | * | 9/1995 | Bacon | 128/200.14 |
| 5,613,489 A | * | 3/1997 | Miller et al. | 128/203.28 |
| 5,692,496 A | * | 12/1997 | Casper et al. | 128/203.15 |
| 5,694,920 A | | 12/1997 | Abrams et al. | |
| 5,740,794 A | * | 4/1998 | Smith et al. | 128/203.15 |
| 5,755,221 A | * | 5/1998 | Bisgaard | 128/203.15 |
| 5,823,183 A | * | 10/1998 | Casper et al. | 128/203.15 |
| 5,875,776 A | * | 3/1999 | Vaghefi | 128/203.15 |
| 5,918,594 A | | 7/1999 | Asking et al. | |
| 5,988,163 A | * | 11/1999 | Casper et al. | 128/203.15 |
| 6,003,512 A | | 12/1999 | Gerde | |
| 6,006,747 A | | 12/1999 | Eisele | |
| 6,026,809 A | | 2/2000 | Abrams et al. | |
| 6,029,662 A | | 2/2000 | Marcon | |
| 6,125,844 A | * | 10/2000 | Samiotes | 128/200.23 |
| 6,176,234 B1 | * | 1/2001 | Salter et al. | 128/200.18 |
| 6,209,538 B1 | * | 4/2001 | Casper et al. | 128/203.15 |
| 6,223,746 B1 | | 5/2001 | Jewett et al. | |
| 6,257,233 B1 | * | 7/2001 | Burr et al. | 128/203.15 |
| 6,318,361 B1 | * | 11/2001 | Sosiak | 128/200.23 |
| 6,325,062 B1 | * | 12/2001 | Sosiak | 128/203.25 |
| 6,422,234 B1 | * | 7/2002 | Bacon | 128/200.14 |
| 6,425,392 B1 | * | 7/2002 | Sosiak | 128/200.23 |
| 6,681,767 B1 | * | 1/2004 | Patton et al. | 128/203.15 |

* cited by examiner

*Primary Examiner*—Aaron J. Lewis
(74) *Attorney, Agent, or Firm*—Frommer Lawrence & Haug LLP; Ronald R. Santucci

(57) ABSTRACT

A breath acutated dry powder inhaler having a housing, a source of pressurized air, transfer valve which allows the release of pressurized air so as to act upon at least one dose of medicament whereupon when a user inhales through a mouthpiece it causes the transfer valve to release the pressurized air which causes the dose to be discharged through the mouthpiece to the user.

8 Claims, 2 Drawing Sheets

BREATH ACTUATED DRY POWDER INHALER

BACKGROUND OF THE INVENTION

1. Field of the Invention

This invention relates to a medicament inhaler, and more particularly to a dry powder medicament inhaler activated by the breathing action of the user operable with pressurized air to emit a metered plume of dry powder particles.

2. Brief Description of the Prior Art

Dry powder inhalers are devices where a predetermined dose of medicament, either alone or in a blend with some carrier like lactose, is released as fine mist of dry powder for inhalation. These systems differ significantly from multi-dose inhalers and nebulizers in that they do not contain any liquid media (e.g. propellant or water). The drug is formulated in a manner so that it readily disperses into particles of respirable size range (i.e. $\leqq 10\ \mu m$).

Single unit dose dry powder inhaler devices are known, including some which contain multiple chambers and a selector element for releasing a dose from one chamber at a time. Relevant aspects in the designs of these devices include: establishing the correct dosage size in the device; preserving such dose from humidity and other deleterious environment elements; and delivery of the dose in a preferred particulate size within the discharge air flow.

Stated otherwise, the concerns are charging (filling) the device and storage, release, and delivery of the dose. The stored powder is, by necessity, compacted into a very small volume in an essentially solid state capsule. One of the prominent challenges encountered in design of these systems has been the breakup, or de-agglomeration, of the aggregate powder dose into a plume of fine particles which are well disbursed in the air flow. Several such devices have been developed which use a variety of methods to accomplish this end.

For example, U.S. Pat. No. 5,694,920 describes an inhalation device. Powdered medicament is stored in a blister well that is carried in a roll housed in a cartridge. Once the blister well is opened, a vibrator de-aggregates the powder in the well and keeps the powder in a fluidized state. An electrostatic plate attracts smaller particles of the powder towards the plate, where they are introduced into an air stream and carried toward a mouthpiece.

Another example is U.S. Pat. No. 6,026,809 which describes an inhalation device that utilizes vibration to facilitate suspension of a powder in a gas. A piezoelectric vibrator is used to vibrate the powder, thereby de-aggregating the powder for optimal suspension in an air stream. A controller is provided for controlling the supply of actuating electricity to the vibrator.

U.S. Pat. No. 5,033,463 describes a multi-dose inhaler for medicaments in powder form. The powder is stored in a container in the inhaler. A certain quantity of powder is withdrawn from the container and conveyed to a dispensing position by a cup. A plunger moves the powder to a mixing unit. Inhalation causes an impeller in the mixing unit to rotate, thereby mixing air and powder before it enters a user's mouth or nose. Vibrations may be used to facilitate dropping the powder from the container to the cup.

U.S. Pat. No. 6,006,747 describes a dry powder inhaler. The inhaler includes a housing, a cartridge containing medicine supported on the housing, a lid pivotally mounted on the housing, and a mixing chamber. An impeller within the mixing chamber mixes air and the drug before they are inhaled into a patient's lungs.

U.S. Pat. No. 5,918,594 describes an inhaling device capable of breaking down aggregates of powdered medicament to provide particles within the respiratory range. A magazine contains a dose. A de-agglomerating device is disposed in the air flow of the dose. The de-agglomerating device is made of opposing surfaces oriented obliquely to a longitudinal direction of the air flow path. When a patient inhales on a mouthpiece, the dose is drawn through the de-agglomerating device.

U.S. Pat. No. 6,003,512 describes an apparatus for aerosolizing and dispensing powders. A dose is placed into a chamber for mixing with pressurized air to break up large particles. The dose may be supplied at each administration, or the apparatus may contain a dose reservoir from which individual doses are supplied to the chamber. The dose mixture is moved through an ejecting conduit and into an exit nozzle. The exit nozzle has a sudden increase in diameter to break the pressurized agglomerates into a fine aerosol.

U.S. Pat. No. 6,029,662 describes a compressed air powder inhaler. Powder is stored in a magazine. Powder from the magazine is mixed with compressed air from an air chamber. The powder is fragmented by the flow of air and then by passing through a grille. The release of the compressed air is triggered by a patient sucking on a mouthpiece.

U.S. Pat. No. 6,223,746 describes a metered dose inhaler and pump for delivery of an active compound without the need for a pressurized active compound container.

It is seen from the foregoing that there are many existing devices which can be actuated by the inhalation of the user; which de-agglomerate stored dry powder medicament; which provide medicament to the user in a metered dosage and which are portable. However, there is always a desire to improve upon or make available alternative operating devices. Such a device should be able to accomplish these ends in an effective yet simple and possibly less costly manner than that of other designs which may be available.

SUMMARY OF THE INVENTION

It is therefore a principal object of the present invention to provide an inhaler which reliably and consistently delivers a desired dose of dry powder medicament to a user in a reasonably short period of time.

It is a further object of the present invention to provide an inhaler which administers metered doses of dry powder medicament to the user.

It is a still further object of the present invention to provide an inhaler for dispensing dry powder medicament where the device is activated by the inhalation of the user.

It is therefore a still further object of the present invention to provide an inhaler which is portable in size.

It is therefore a still further object of the present invention to provide an inhaler where each dry powdered dose is individually contained and dispersed.

A yet further object of the present invention is to provide an inhaler where after each use, a new dose is automatically indexed for the next use of the inhaler.

To attain the objects described, there is provided a device which is a breath activated dry powder inhaler. The inhaler comprises the major components of a body, mouthpiece, pressurizing and release mechanism, and a dose container, such as that, for example, set forth in co-pending U.S. patent application Ser. No. 09/756,313 filed Jan. 8, 2001 entitled "Dry Powder Inhaler", the disclosure of which is incorporated herein by reference.

The breath actuated dry powder inhaler operates as follows. Initially, the use manually depresses and releases the pump piston of the air pump which pressurizes air in a chamber. In this regard, the depressing action of the user compresses and forces air from a primary air chamber into a secondary air chamber. A valve between the chambers maintains the secondary chamber in a pressurized state. A transfer valve mechanism blocks a path of flow from the secondary chamber to a conduit connected to the dose to be dispensed.

When the user inhales through the mouthpiece, it creates a pressure differential across the transfer valve mechanism. As a threshold differential is reached, pressurized air from the secondary chamber causes the transfer valve mechanism to open creating a flow of pressurized air to the dose container. The pressurized air dispenses a flow of powder from the dose container whilst de-agglomerating and fluidizing the stored powder in the air flow. The powder then exits the mouthpiece to the user.

BRIEF DESCRIPTION OF THE DRAWINGS

Thus by the present invention its objects and advantages will be realized, the description of which should be taken in conjunction with the drawings, wherein.

DETAILED DESCRIPTION OF THE PREFERRED EMBODIMENTS

Figure 1:
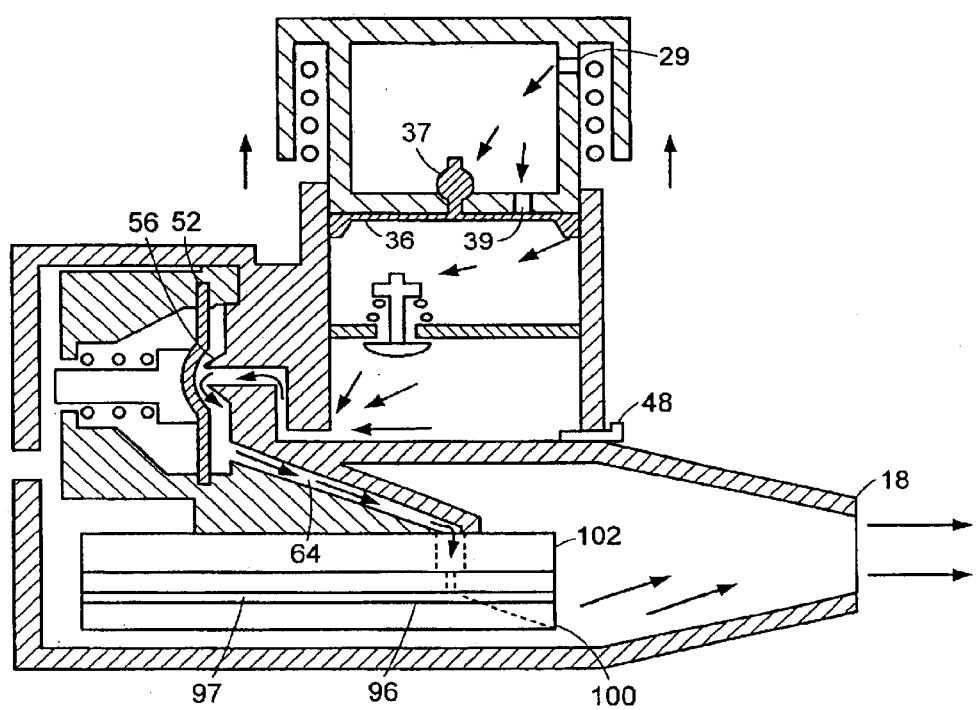
FIG. 1 is a side cross-sectional view of the breath actuated dry powder inhaler shown prior to pressurization, incorporating the teachings of the present invention.

Initially, it should be noted that the present inhaler or dispenser is particularly effective in dispensing dose units as set forth and described in the aforenoted application. Generally, and with regard to that set forth in that application, dose storage and de-agglomeration are critical elements of dry powder inhaler devices. Combining the storage and de-agglomeration elements into a single component, which accommodates both functions is desirable from a device engineering perspective, provided the powder is well protected from ambient conditions, particularly humidity, whilst achieving performance targets for drug delivery through the device. The dry powder dose container in said application accomplishes this storage/de-agglomeration and delivery. The present device, when combined with properly stored doses and the mechanism of dispensing along with breath actuation by the user produces a plume of dry powder with particle sizes in the respirable range.

Note, however, while the present device is particularly suited for dispensing dose units stored in the device described in the patent application aforesaid, implementation with different types of storage devices suitable for the purpose should be apparent to one skilled in the art.

Turning now more particularly to the drawings wherein like numerals refer to like elements throughout the several views, FIG. 1 is a side cross-sectional view of the breath actuated dry powder inhaler 10 of the present invention shown in its starting or unprimed position. The inhaler 10 is generally defined by a plunger 12 contained in a hollowed cylinder body 14 having an exterior wall 16, mouthpiece 18, lower wall 20, valve wall 22, and upper wall 24.

Plunger 12 is a cap in which the wall 26 is sized to slide along the exterior wall 16 when pressure is applied by the user. Integral to the wall 26 of plunger 12 is a hollow air pump piston 28 having an inlet port 29. The air pump piston 28, when downward force is applied to the plunger 12, pressurizes air in the primary air chamber 30 eventually forcing pressurized air into the secondary air chamber 32.

The primary air chamber 30 is generally defined by lower base 34, a flexible piston seal 36 which is mounted on the piston 28 via a resilient snap 37, bleed orifice 39 and interior wall 38. An aperture 40 is located in base 34. Aperture 40 is sized to accommodate check valve 42 generally illustrated. The check valve 42 shown comprises a spring 43 and lifting disc type valve with a plugging stop 44. Of course, as will be apparent to a skilled worker, other type valves suitable for purpose may be utilized.

Upon depressing plunger 12, pressurized air is forced from chamber 30 through aperture 40 acting against the spring 43 which is biasing valve 42 closed.

From aperture 40, the pressurized air enters secondary air chamber 32. Secondary air chamber 32 is generally defined by base 34, lower section 45, and interior wall 38. Note that, generally shown at 48 is a mechanism to indicate that chamber 32 is charged or pressurized. This can be a pressure gauge or other means such as a pop-out device upon pressurization of a sufficient threshold that indicates to the user that the device is primed and ready to be activated.

Contemporaneously, pressurized air is also contained in transfer passage or conduit 50 which leads from the chamber 32 to the face of a diaphragm 52. Side wall 54 faces diaphragm 52 and includes an orifice lip 56. Orifice lip 56 is a tapered frustonconical protrusion integral to side wall 54. Orifice lip 56 is sealed by diaphragm 52.

Diaphragm 52 may be a flat circular elastomeric section which is on the face of and possibly clamped to the end of transfer valve 66 which is supported in the device 10. About periphery 68 of diaphragm 52, it is sealingly fixed from movement. A transfer port 64 connects valve cavity 69 to a dose container 70. The transfer valve 66 is spring loaded via spring 74 to bias the diaphragm 52 against orifice lip 56 effecting a sealing thereof whilst chamber 32 is being charged. While a spring is shown, any other type biasing means suitable for the purpose may also be used.

Cavity 76 provides operating space for the transfer valve 66 and allows communication with the interior of the inhaler 10, particularly the mouthpiece 18, for purposes that will be described.

Bottom interior wall 78 has an attachment section 80 for the dose container 70. Attached at an outlet 84 of transfer port 64 is the dose container 70. Exterior wall 22 contains an air inlet 92 which provides a source of air to the user via the interior of the inhaler 10 and out the mouthpiece 18.

As aforesaid, the pending U.S. patent application entitled "Dry Powder Inhaler" filed on Jan. 8, 2001, Ser. No. 09/756,313 incorporated herein by reference is the preferred dose container. Its construction and operation is set forth in that application and will not be repeated in detail herein. However, FIG. 6 thereof provides for a rotating dose container having a plurality of doses thereon. The rotating mechanism (not shown) may be automatic or manual and may include an indexing means to indicate doses remaining or taken. Such mechanisms are numerous in the field and the implementation thereof will be readily apparent to a skilled worker in the art. Also, other substitute dose containers suitable for the purpose may also be utilized.

Briefly, however, describing the illustrated dose container 70, it includes a bottom substrate 94 defining therein an exit channel, above that a vibrating sheet substrate 96, a dose storage substrate 97 and an air inlet substrate 98. Disposed in mouthpiece 18 is an exit discharge opening 100 and at the top of the dose container 70 is an inlet opening 102 which sealably aligns with outlet 84.

Figure 2:
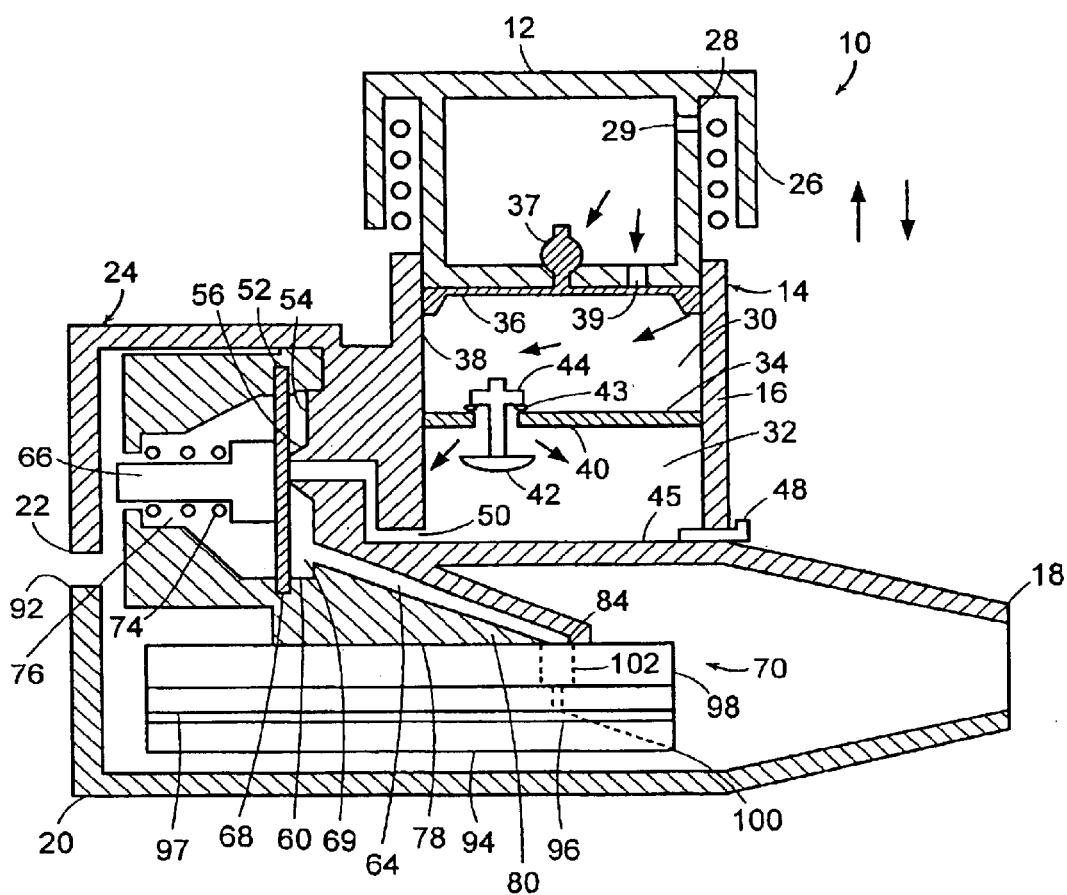
FIG. 2 is a side cross-sectional view of the breath actuated dry powder inhaler prior to dispensing, incorporating the teachings of the present invention.

Turning now to FIG. 2, it depicts the inhaler 10 in its operational mode. When the user inhales through mouthpiece 18, a vacuum is created inside causing a pressure differential across diaphragm 52. As a predetermined threshold vacuum is exceeded, pressurized air begins to leak past orifice 56 pressurizing transfer port 64. The continuation of leaking pressurized air causes diaphragm 52 to be forced backward fully exposing orifice 56. The pressurized air then flows freely through transfer port 64 to the inlet opening 102. All of this happens very quickly.

The pressurized shot of air breaks open a seal in the dose storage substrate 97 containing powdered medicament blowing the medicament dose pass the vibrating sheet substrate 96. The vibrating sheet substrate 96 whips or vibrates as result of the application of compressed air. This whipping motion of the vibrating sheet substrate 96 effectively breaks the powder carried by the air-flow into smaller and more uniform particles, thus de-agglomerating the solid into a fine powder. The air flow over the sheet of the vibrating sheet substrate 96 creates a standing wave that has the effect of metering the dose into the air stream. The fine powder medicament flows through the exit discharge opening 100 and assisted by the inhalation of the user, the dry powder medicament exits the mouthpiece 18.

Upon return of the inhaler 10 to its starting position shown in FIG. 1 as aforesaid, inlet port 29 allows air to be drawn in via bleed orifice 39 and around seal 36 which defects slightly, so as to allow the piston 12 to return to its original position. Also, after the dose has been dispensed, the dosing container 70 or just substrate 97 thereof can be manually or automatically indexed. Manual or automatic indexing of the dose container 70 prepares the inhaler 10 for its next use. In addition, the pressure indicator mechanism would now indicate that the device needs to be primed.

Thus by the present invention its objects and advantages are realized and although a preferred embodiment has been disclosed and described in detail herein, its scope should not be limited thereby rather its scope should be determined by that of the appended claims.

What is claimed is:

1. An inhaler actuated by the inhalation of the user and operable with a source of pressurized air comprising:
   a housing;
   a primary air chamber wherein air is pressurized by the user;
   a secondary air chamber communicating with said primary air chamber wherein said pressurized air is stored for use after exiting the primary air chamber;
   a transfer valve wherein said transfer valve controls passage of the pressurized air stored from said secondary air chamber;
   a mouthpiece;
   a passageway communicating said mouthpiece with said transfer valve;
   a dosing container contained in said housing containing at least one dose of medicament;
   a conduit in said housing allowing communication between the transfer valve and the dose container; and
   means for dispensing medicament, said means being activated by a user's inhalation without other manual action which creates a vacuum in said housing thereby actuating the transfer valve releasing said pressurized air from the secondary air chamber to the conduit to the dose container expelling said dose of medicament into and out of the mouthpiece thereby administering a dose of medicament from the dose container to the user.

2. The inhaler of claim 1 further including a check valve in the passage between the primary air chamber and the secondary air chamber wherein said check valve allows the pressurized air from the primary air chamber to enter the secondary air chamber.

3. The inhaler of claim 1 further including an indicator, wherein said indicator indicates pressurized air within the secondary air chamber.

4. The inhaler of claim 1, wherein said dose container comprises a plurality of dry powder doses and administers said medicament to the user in metered doses.

5. The inhaler of claim 1 further including an air pump piston, wherein said air pump piston pressurizes air in said primary air chamber.

6. A method of dispensing medicament comprising the steps of:
   providing the inhaler of claim 1;
   inhaling through the mouthpiece;
   actuating the transfer valve thereby releasing pressurized air from the secondary air chamber;
   supplying the pressurized air to the dose container;
   applying the pressurized air to a medicament dose within said dose container; and
   forcing said dose through an exit channel into the mouthpiece thereby dispensing said medicament to the user.

7. The method of claim 6 further including the steps of providing a dose container having at least one dose of dry powder medicament, de-agglomerating said medicament dose whilst blowing said dose through an exit channel and into the mouthpiece of said housing whereby said medicament dose is dispensed to the user.

8. The method of claim 7 wherein said container includes a plurality of doses each of which is metered.

* * * * *